| United States Patent [19] | [11] Patent Number: 4,528,370 |
| Lai | [45] Date of Patent: Jul. 9, 1985 |

[54] POLYSUBSTITUTED 2-MORPHOLONES

[76] Inventor: John T. Lai, 663 Tollis Pkwy., Broadview Heights, Ohio 44147

[21] Appl. No.: 367,631

[22] Filed: Apr. 12, 1982

[51] Int. Cl.$^3$ .......................................... C07D 265/32
[52] U.S. Cl. .................................................. 544/173
[58] Field of Search ........................................ 544/173

[56] References Cited

U.S. PATENT DOCUMENTS 3,073,822  1/1963  Schultz et al. ..................... 544/173

OTHER PUBLICATIONS

Koch et al., *J. Amer. Chem. Soc.*, vol. 97 (1975), pp. 7285–7288.

*Primary Examiner*—Robert W. Ramsuer

[57] ABSTRACT

An essentially single stage reaction has been discovered in which a disubstituted ethanolamine, that is, a 2,2'-substituted-2-aminoethanol, may be reacted with a haloform and a carbonyl containing compound selected from the group consisting of monoketones and benzaldehyde, in the presence of an alkali metal hydroxide, and optionally in the presence of a phase transfer catalyst, to produce an alkali metal hydroxyethylaminoacetate ("HEAA") which has N-adjacent C atoms on which there are a total of at least three substituents (hence "polysubstituted"), and one or both pairs of substituents on each N-adjacent C atom may be cyclized. The HEAA may be cyclized by the action of a mineral acid to produce a 2-morpholone hydrochloride which is characterized by having a total of at least three substituents on the N-adjacent C atoms of the ring. The 2-morpholone so produced may be reduced to a polysubstituted aminodiol. The aminodiol so produced may be cyclized with an alkane sulfonic acid to yield a polysubstituted morpholine which could not otherwise have been made. The aminodiol may also be alkylated to produce diethers with polysubstituted N-adjacent C atoms. If the aminodiol is tosylated, a polysubstituted crown ether is produced with plural polyalkylene groups. The foregoing HEAA and related compounds are used as u-v light stabilizers in novel compositions in which a small but effective amount of one or more of the HEAA and related compounds is incorporated, in an amount sufficient to produce desirable stabilization against degradation by u-v light in a wide variety of organic materials.

2 Claims, No Drawings

POLYSUBSTITUTED 2-MORPHOLONES

BACKGROUND OF THE INVENTION

Substituted morpholines are commercially available and widely used as dispersing agents for waxes and the like. These morpholines are easily prepared from substituted diethanolamines by closing the ring.

Substituted morpholin-2-ones ("2-morpholones") on the other hand, are relatively uncommon compounds known to be useful in pharmaceutical preparations, and not easily prepared. Such 2-morpholones are conventionally prepared as described in *Heterocyclic Compounds*, Vol 6, by Robert C. Elderfield in the chapter entitled "The Monocyclic Oxazines", John Wiley & Sons, Inc. New York (1957).

More recently a mixture of 2-morpholone dimers was produced by irradiation of 5,6-dihydro-3,5,5-trimethyl-1,4-oxazin-2-one in 2-propanol solvent 15° C. (see "An Unusually Weak Carbon-Carbon Single Bond" by Koch, T. H., Olesen, J. A., and DeNiro, J. in *J. Am. Chem. Soc.* 97:25, 7285-80, 1979). The mixed dimers were found to be thermally unstable in solution, and in the presence of oxygen the dimer was rapidly oxidized to 5,6-dihydro-3,5,5-trimethyl-1,4-oxazin-2-one; but prolonged heating in the absence of oxygen gave a mixture of the foregoing oxazine and 3,5,5-trimethyl-morpholin-2-one ("morpholone"). The morpholone so formed must, as a result, have only one substituent on the C atom in the "3" position ($C^3$) of the ring. Though there are two alkyl substituents on the $C^5$ atom of the ring, it will be realized that the substituents on this $C^5$ atom are necessarily lower alkyl. Thus the prior art monomer is a tri-substituted morpholone with only a single substituent on the $C^3$ atom, and it may not be tetra-substituted with alkyl substituents.

Still more recently, a 5,5-dimethyl-3-phenyl-2-morpholone was prepared which was somewhat unstable and existed in equilibrium with a ring-opened product identified as methyl-2-phenyl-2-(1,1-dimethyl-2-hydroxyethyl)aminoacetate (see "Electron-Transfer Chemistry of the Merostabilized 3,5,5-Trimethyl-2-morpholinon-3-yl Radical" by Burns, J. M., Wharry, D. L. and Koch, T. H., *J. Am. Chem. Soc.*, 103, 849–856, 1981).

Research probing the reactions of the dimers resulted in the knowledge that a mixture of meso and dl dimers heated with 2,2'-azobis(2-methylpropionitrile) produced [2'-(2'-cyanopropyl)]-3,5,5-trimethylmorpholin-2-one. This cyanoalkyl substituted-trimethylmorpholone and the phenyl-substituted-trimethylmorpholone are the only tetra-substituted 2-morpholones known. The substituents on the N-adjacent C atoms cannot be changed because of the recognized relative instability of the lactone ring. For example, it has been found that this ring can neither be reduced nor oxidized without opening it. Thus, I know neither of any tri- or tetra-substituted morpholines which maybe derived from known 2-morpholones, nor of any 2-morpholones which can be derived by replacement of the cyanoalkyl or phenyl substituents on the $C^3$ atom by another substituent without disrupting the lactone ring. Nor do I know of any method for preparing a $C^3$-cyanoalkyl-substituted-2-morpholone or $C^3$-phenyl-substituted-2-morpholone, with other than lower alkyl substituents on the $C^5$ atom of the lactone ring.

Stated differently, it was not heretofore known how polysubstituted compounds may be prepared which have either (a) three substituents which are not lower alkyl, or, (b) three substituents, one of which on $C^3$ is phenyl or cyanoalkyl, and at least one of the remaining two substituents on the other N-adjacent C atom is not alkyl, or, (c) four substituents all of which may be alkyl, on the (combined) N-adjacent C atoms. The term "polysubstituted" is specifically used in this specification to connote that in the claimed compounds of this invention, a total of three or more substituents is necessarily present on the two N-adjacent C atoms, combined; and, two substituents, which may be cyclized, are always present on the $C^3$ atom when the compound is a 2-morpholone. In this sense, it will be recognized that if each of the substituents on the one N-adjacent C atom are cyclic substituents, and the substituents on the other N-adjacent C atom are not, then there are a total of four substituents; there are also four substituents if the two substituents on each N-adjacent C atom are together cyclized.

The problem with preparing polysubstituted 2-1-morpholones carries over to the preparation of polysubstituted morpholines. For example, it is known that reductive alkylation of $HOCH_2C(CH_3)_2NH_2$ with $CH_3COCH_2OH$ yields $[(HOCH_2C(CH_3)_2]NH[CH(CH_3)CH_2OH]$ which upon cyclization by heating with conc $H_2SO_4$ produces 3,5,5-trimethylmorpholine (see 112872h Chem. Abstr. Vol 71, pg 374, 1979), but this approach cannot produce a trimethyl-2-morpholone.

The key to providing three or more substituents on the combined N-adjacent C atoms, is to provide the polysubstituents on the C atoms before the ring is closed. Only a few such polysubstituted compounds are known. In these known compounds, only specific substituents may be present because of the manner in which the compounds are necessarily prepared. Such compounds are 3-[2'-(2'-cyanopropyl)]-3,5,5-trimethylmorpholin-2-one, prepared as described in the Koch et al. articles, supra; and, 5,5-dimethyl-3-phenyl-2-morpholinone, prepared as described in the Burns et al article, supra. Though sodium hydroxyethylaminoacetate is easily prepared, and two substituents may be made on one or the other N-adjacent C atom, or, one substituent may be made on one and also (one) on the other N-adjacent C atom, polysubstituted hydroxyethylaminoacetates ("HEAA" for brevity) having three or more substituents have not been known or made because of the steric hindrance problems, inter alia. Further, though polysubstituted aminodiols such as $[HOCH_2C(CH_3)_2]NH[CH(CH_3)CH_2OH]$ are known, I know of no apparently operable method for converting such aminodiols to N-hydroxyalkylamino acids. As a result, tri-substituted or tetra-substituted N-adjacent C atoms of an alkali metal hydroxyethylaminoacetate are not known.

Hindered amines, to which general class the compounds of this invention belong, are known to have utility as u-v light stabilizers in synthetic resins subject to actinic radiation. However, not all hindered amines are effective stabilizers against u-v light degradation in normally solid polymers. Some hindered amines are thermally unstable at as low as 100° C. which precludes their use in any organic material which is processed at or above that temperature. Further, particularly with polysubstituted heterocyclic ring compounds, N atoms in the ring are known to have a beneficial effect but there is no more reason to expect that a polysubstituted morpholone might be effective than there is to believe that a polysubstituted thiomorpholine might be effective. More particularly, it was known that dimers of 5,6-dihydro-3,5,5-1-trimethyl-1,4-oxazin-2-one are photoreductive and thermally unstable in solution when heated to 80° C., and that in solution, these dimers exist in equilibrium with a radical at room temperature (Koch et al, supra). Therefore, it was quite surprising that a polysubstituted 2-morpholone or a polysubstituted related compound, would provide excellent u-v light stability.

Because of the unpredictability of the effectiveness of various hindered amines solely based on their (hindered) structure, much effort has been expended to synthesize hindered amines which must then be tested for possible utility as u-v light stabilizers. One of the synthesis is described in an article titled "Hindered Amines. Novel Synthesis of 1,3,3,5,5-Pentasubstituted 2-Piperazinones" by John T. Lai in J. Org. Chem. 45, 754 (1980). The concept of retaining the "2-keto" ring structure of a heterocyclic ring containing at least one N atom was the basis upon which the search for effective 2-morpholones was initiated. The necessity of providing more than two substituents on the N-adjacent C atoms spurred the discovery of the application of a "ketoform synthesis" to solve the problem. This invention derives from further research in the field of the synthesis of hindered amines, and an evaluation of their effectiveness as u-v light stabilizers.

Hindered amines of the prior art are generally complex compounds not prepared with notable ease, and their properties, particularly their compatibility in various synthetic resins, is difficult to predict. Apparently small differences in structure, result in large differences in performance. Prolonged efforts to provide simpler compounds which are relatively easily prepared, have resulted in the 2-keto-1,4-diazacycloalkanes and the 2-keto-1,5-diazacycloalkanes disclosed in U.S. Pat. Nos. 4,190,571 and 4,207,228.

The present invention is particularly directed to (a) novel polysubstituted alkali metal hydroxyethylaminoacetates, (b) a novel synthesis for a polysubstituted alkali metal hydroxyethylaminoacetate, (c) novel compositions in which a polysubstituted alkali metal hydroxyethylaminoacetate is incorporated, (d) novel polysubstituted 2-morpholones, (e) a novel synthesis for polysubstituted 2-morpholones, (f) novel compositions stabilized against u-v light degradation by the presence of a stabilizing amount of the 2-morpholones, (g) novel polysubstituted aminodiols, (h) novel compositions stabilized against u-v light degradation by the presence of a small but effective amount of a polysubstituted aminodiol, (i) novel polysubstituted monoaza crown ethers, (j) synthesis of polysubstituted monoaza crown ethers, (k) novel compositions stabilized against u-v light degradation by the presence of an effective amount a polysubstituted monoaza crown ether, (l) polysubstituted morpholine, (m) synthesis of polysubstituted morpholine by cyclization of an aminodiol with an alkanesulfonic acid, (n) novel compositions stabilized against u-v light degradation by the presence therein of an effective amount of a polysubstituted morpholine, (o) novel polysubstituted aminodiethers, and (p) novel compositions stabilized by the presence therein of an effective amount of a polysubstituted aminodiether.

The synthesis of the novel stabilizers of this invention is facilitated by the peculiar action of certain onium salts in an aqueous alkaline medium, which action facilitates the interaction of an amine nucleophilic agent such as a primary or secondary amine, with chloroform or other trichloromethide generating agent, and a ketone or aldehyde. The organic onium salts of nitrogen, and phosphorus are well known. They are ionized in aqueous solutions to form stable cations. Certain onium salts have provided the basis for phase transfer catalysis in a wide variety of reactions, a recent and comprehensive review of which is contained in Angewandte Chemie, International Edition in English, 16 493–558 (August 1977). Discussed therein are various anion transfer reactions where the onium salt exchanges its original anion for other anions in the aqueous phase. These ion pairs can then enter a water immiscible, organic liquid phase, making it possible to carry out chemistry there with the transported anion, including $OH^-$ ions. Many reactions involving water immiscible solutions of various simple organic molecules have been described. Though the use of phase transfer catalysts facilitate the cyclization of an appropriately sterically hindered branched chain amine having proximate primary and secondary amine groups amongst plural amine groups in the chain, the reaction has also been found to proceed, though relatively slowly, by simply using a large excess of the ketone or aromatic aldehyde either of which is the the essential carbonyl containing compound which contributes the carbonyl group to the 2-position of the diazacycloalkane ring.

A phase transfer catalyzed reaction known as the "ketoform reaction" is disclosed in U.S. Pat. No. 4,167,512, which proceeds by virtue of a phase transfer catalyzed reaction mechanism in which an amine, a haloform and a carbonyl containing ("carbonyl") compound are separate reactants. This reaction is illustrated in one particular example by the reaction of a N,N'-alkyl substituted ethylene diamine with acetone and chloroform; and, in another example, with o-phenylene diamine reacted with cyclohexanone and chloroform. The reaction product in each example is a 2-keto-1,4-diazacycloalkane.

Though both ketones and aldehydes are taught as being effective reactants in the ketoform reaction, it has now been discovered that only ketones and benzaldehyde are effective in the formation of HEAA. Accordingly, my present invention is a particular adaptation of the ketoform reaction to the preparation of alkali metal HEAA, and several successor compounds derived therefrom, including 2-morpholones, aminodiols, monoaza crown ethers, and morpholines, all of which are polysubstituted, and are collectively referred to herein as "HEAA compounds" for brevity.

SUMMARY OF THE INVENTION

An essentially single stage reaction has been discovered in which a disubstituted ethanolamine, that is, a 2,2'-disubstituted-2-aminoethanol, may be reacted with a haloform and a carbonyl containing compound selected from the group consisting of monoketones and an aromatic monoaldehyde (araldehyde) having from 7 to about 9 carbon atoms, in the presence of an alkali metal hydroxide, and optionally in the presence of a phase transfer catalyst, to produce an alkali metal hydroxyethylaminoacetate ("HEAA") which has N-adjacent C atoms on which there are a total of at least three substituents (hence "polysubstituted"), and one or both pairs of substituents on each N-adjacent C atom may be cyclized.

It has further been discovered that a polysubstituted alkali metal HEAA may be cyclized by the action of a strong acid, for example concentrated HCl, to produce a 2-morpholone hydrochloride which is characterized by having a total of at least three substituents on the N-adjacent C atoms of the ring. By reaction with triethylamine, or other base, a polysubstituted 2-morpholone is produced. Novel polysubstituted 2-morpholones are produced in which the $C^3$ position is disubstituted from a wide choice of substituents. If the $C^3$ position is monosubstituted with phenyl then the $C^5$ position is substituted with at least one substituent which is not lower alkyl; if the $C^3$ position is disubstituted and one of the two substituents is cyanoalkyl, then the $C^5$ position is substituted with at least one substituent which is not lower alkyl.

It has still further been discovered that the polysubstituted 2-morpholones so produced may be reduced by reaction with $LiAlH_4$, diborane, or $H_2$ under pressure in the presence of Raney's nickel catalyst, to a polysubstituted aminodiol.

It has also been discovered that the aminodiol so produced may be cyclized with an alkane sulfonic acid to yield a polysubstituted morpholine which could not otherwise have been made, and can now be made only by this cyclization reaction.

It has also further been discovered that the aminodiol so produced may be conventionally alkylated to produce diethers with polysubstituted N-adjacent C atoms. If the aminodiol is reacted with a polyalkyleneglycol ditosylate, a polysubstituted crown ether is produced with plural polyalkylene groups.

It is therefore a general object of this invention to provide novel polysubstituted alkali metal hydroxyethylaminoacetates ("HEAA"), and novel compounds related thereto, or derived therefrom, all of which are collectively referred to herein as "HEAA compounds"; to provide processes for producing the novel compounds; and, to provide novel compositions in which a small but effective amount of one or more of the HEAA compounds is incorporated, optionally in addition with antioxidant synergists, pigments, and other known compounding ingredients, in amounts sufficient to produce desirable stabilization against degradation in a wide variety of organic materials.

DETAILED DESCRIPTION OF PREFERRED EMBODIMENTS

The polysubstituted structure of the various stabilizer compounds prepared by the syntheses described herein, is derived by virtue of an adaptation of the ketoform synthesis. This adaptation permits the preparation of a polysubstituted HEAA without the formation of isocyanides. As is well known, primary amines react with chloroform in the presence of NaOH in the carbylamine reaction which is a delicate test for the presence of a primary amine because of the powerful odor of the ioscyanides formed. No powerful odor of isocyanide is detected in the adaptation of the ketoform reaction as used in this invention.

The HEAA is preferably tetra-substituted, though tri-substituted HEAA also have good u-v stabilization effects in transparent, translucent or lightly colored synthetic resins. Despite the seemingly simple structure of alkali metal HEAA which have at least three substituents on the N-adjacent carbon atoms, these HEAA to my knowledge, can be prepared by no other method than that described hereinbelow.

The structure of an alkali metal HEAA is as follows:

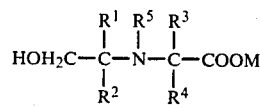

wherein,
- $R^1$, $R^2$, $R^3$ and $R^4$ are independently selected from the group consisting of hydrogen, aryl, alkyl having from 1 to about 24 carbon atoms, cycloalkyl having from 5 to about 7 carbon atoms, aralkyl having from 7 to about 20 carbon atoms, cyanoalkyl having from 2 to about 12 carbon atoms, ether having from 4 to about 18 carbon atoms, and hydroxyalkyl having from 1 to about 18 carbon atoms;
- $R^1$ and $R^2$ together, or $R^3$ and $R^4$ together, or each pair, may be cyclized forming a ring having from about 5 to about 8 carbon atoms;
- except that not more than one of $R^1$, $R^2$, $R^3$ or $R^4$ may be hydrogen, and no more than three of $R^1$, $R^2$, $R^3$ and $R^4$ may be cyclic;
- $R^5$ is selected from hydrogen, oxygen, hydroxyl and alkyl having from 1 to about 24 carbon atoms; and,
- M represents an alkali metal.

Process for preparing an alkali metal HEAA

The starting material is a 2,2'-substituted-2-aminoethanol represented by the following structure:

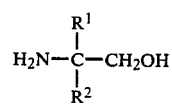

wherein $R^1$ and $R^2$ have the same connotation as hereinabove, and $R^1$ and $R^2$ may together be cyclized forming a ring having from about 5 to about 8 carbon atoms.

As will presently be evident, a wide range of substituents may be made without undue difficulty, and the choice of substituents in large part, determines the properties of the compound as a u-v stabilizer. This aminoethanol may be only mono-substituted, depending upon the choice of a ketone as a reactant in the reaction to be described hereinbelow, but best results are obtained when the aminoethanol is di-substituted, which includes the case where $R^1$ and $R^2$ are cyclized. Since the aminoethanol is a primary amine it will be apparent that any substituent desired on the N atom will have to be made after the formation of the polysubstituted alkali metal hydroxyethylaminoacetate ("HEAA") as set forth hereunder.

This aminoethanol is reacted with (i) at least one molar equivalent of a haloform selected from the group consisting of chloroform and bromoform, and (ii) at least one molar equivalent of a carbonyl containing compound selected from the group consisting of monoketones and an aromatic monoaldehyde ("araldehyde") which may be ring substituted having from 7 to about 9 carbon atoms, optionally (iii) in the presence of a phase transfer catalyst, and, necessarily with (iv) at least one molar equivalent of an alkali metal hydroxide so as to form the alkali metal HEAA. The preferred temperature of the reaction with a ketone is in the range from about −10° C. to about 30° C. at ambient pressure, and from about 10° C. to about 60° C. with an araldehyde. Some reactions may be preferably carried out under elevated pressure, and others under vacuum, but in general, pressure plays only its expected role in the progress of the reaction.

The HEAA compounds of this invention are hindered amines and undergo the expected reactions which hindered amines are known to undergo. For example, the hydrogen on the N atom may be replaced with an alkyl group having from 1 to about 24 carbon atoms, by conventional alkylation; or, the H may be replaced by oxygen by reaction of the HEAA with metachloroperbenzoic acid; in turn, it will be appreciated, that the alkyl group or oxygen so introduced on the N atom, may be further reacted, conventionally, to give additional substituents.

Process for preparing polysubstituted 2-morpholones

The alkali metal HEAA prepared as described hereinabove may be cyclized with a cyclization agent to yield a 2-morpholone which retains the substituents on the N-adjacent atoms. The polysubstituted 2-morpholone has the following structure:

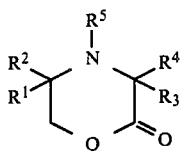

wherein, $R^1$, $R^2$, $R^3$ and $R^4$ are independently selected from the group consisting of aryl, alkyl having from 1 to about 24 carbon atoms, cycloalkyl having from 5 to about 7 carbon atoms, aralkyl having from 7 to about 20 carbon atoms, cyanoalkyl having from 2 to about 12 carbon atoms, ether having from 4 to about 18 carbon atoms, and hydroxyalkyl having from 1 to about 18 carbon atoms;

$R^1$ and $R^2$ together, or $R^3$ and $R^4$ together, or each pair, may be cyclized forming a ring having from about 5 to about 8 carbon atoms; and, $R^5$ is selected from hydrogen, oxygen and alkyl having from 1 to about 24 carbon atoms, and hydroxyl; except that not more than one of $R^1$, $R^2$, $R^3$ or $R^4$ may be hydrogen; and no more than three of $R^1$, $R^2$, $R^3$ and $R^4$ may be cyclic; further, if one of $R^3$ and $R^4$ is H or lower alkyl having from 1 to about 6 carbon atoms and the other is phenyl or cyanoalkyl, then at least one of $R^1$ and $R^2$ is not alkyl.

Cyclization is preferably effected by contacting the alkali metal HEAA with strong acid, for example concentrated HCl. The 2-morpholone hydrochloride so formed may then be reacted with triethylamine to remove the HCl and form the 2-morpholone. The temperature at which the reaction is carried out may be in the range from from about −10° C. to about 100° C.

Process for preparing polysubstituted aminodiols

The polysubstituted 2-morpholones prepared as described hereinabove may be reduced with a suitable reducing agent to yield a polysubstituted aminodiol having the structure:

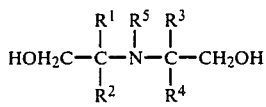

wherein, $R^1$, $R^2$, $R^3$ and $R^4$ are independently selected from the group consisting of aryl, alkyl having from 1 to about 24 carbon atoms, cycloalkyl having from 5 to about 7 carbon atoms, aralkyl having from 7 to about 20 carbon atoms, cyanoalkyl having from 2 to about 12 carbon atoms, ether having from 4 to about 18 carbon atoms, and hydroxyalkyl having from 1 to about 18 carbon atoms;

$R^1$ and $R^2$ together, or $R^3$ and $R^4$ together, or each pair, may be cyclized forming a ring having from about 5 to about 8 carbon atoms; and, $R^5$ is selected from hydrogen, oxygen, hydroxyl and alkyl having from 1 to about 24 carbon atoms; except that not more than one of $R^1$, $R^2$, $R^3$ or $R^4$ may be hydrogen; and no more than three of $R^1$, $R^2$, $R^3$ and $R^4$ may be cyclic.

The reduction of the polysubstituted 2-morpholone may be effected by any conventional reaction such as reduction with diborane, or LiAlH$_4$, or more preferably, with H$_2$ under pressure in the presence of a Raney's nickel catalyst, any of which reactions result in opening of the lactone ring rather than formation of the morpholine. If reduced with LiAlH$_4$ the reactants are dissolved in THF and refluxed for several hours. After cooling, the reaction mixture is neutralized with dilute NaOH solution to yield the aminodiol which is normally solid.

Process for preparing polysubstituted monoaza crown ethers

The polysubstituted aminodiol prepared as described hereinabove may be cyclized so as to include a polyalkylene oxide bridge, by reaction with a polyalkylenediol with terminal leaving groups, so as to yield a monoaza crown ether. This reaction is quite unexpected because it occurs despite the hindrance of the substituents on the N-adjacent atom of the aminodiol. The monoaza crown ether formed upon cyclization is represented by the structure:

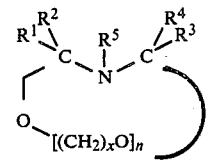

wherein, $R^1$, $R^2$, $R^3$ and $R^4$ are independently selected from the group consisting of aryl, alkyl having from 1 to about 24 carbon atoms, cycloalkyl having from 5 to about 7 carbon atoms, aralkyl having from 7 to about 20 carbon atoms, cyanoalkyl having from 2 to about 12 carbon atoms, ether having from 4 to about 18 carbon atoms, and hydroxyalkyl having from 2 to about 18 carbon atoms;

$R^1$ and $R^2$ together, or $R^3$ and $R^4$ together, or each pair, may be cyclized forming a ring having from about 5 to about 8 carbon atoms; and, $R^5$ is selected from hydrogen, oxygen and alkyl having from 1 to about 24 carbon atoms, and hydroxyl; except that not more than one of $R^1$, $R^2$, $R^3$ or $R^4$ may be hydrogen; and no more than three of $R^1$, $R^2$, $R^3$ and $R^4$ may be cyclic; and, x and n are integers in the range from 2 to 4.

The polyalkylene oxide bridge is preferably introduced into the monoaza crown ether ring by tosylation with a ditosylglycol. Though there may be three methylene groups, most preferred are two, that is, a polyethylene oxide bridge.

Process for preparing polysubstituted morpholines

The aminodiol obtained as described hereinabove may be cyclized by reaction with an alkane sulfonic acid to yield a polysubstituted morpholine having the structure:

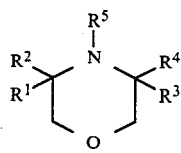

wherein,
R$^1$, R$^2$, R$^3$ and R$^4$ are independently selected from the group consisting of aryl, alkyl having from 1 to about 24 carbon atoms, cycloalkyl having from 5 to about 7 carbon atoms, aralkyl having from 7 to about 20 carbon atoms, cyanoalkyl having from 2 to about 12 carbon atoms, ether having from 4 to about 18 carbon atoms, and hydroxyalkyl having from 2 to about 18 carbon atoms;
R$^1$ and R$^2$ together, or R$^3$ and R$^4$ together, or each pair, may be cyclized forming a ring having from about 5 to about 8 carbon atoms; and,
R$^5$ is selected from hydrogen, oxygen and alkyl having from 1 to about 24 carbon atoms, and hydroxyl;
except that not more than one of R$^1$, R$^2$, R$^3$ or R$^4$ maybe hydrogen; and no more than three of R$^1$, R$^2$, R$^3$ and R$^4$ may be cyclic.

Only an alkane sulfonic acid is effective to cyclize the aminodiol, and lower alkane sulfonic acids having from 1 to about 5 carbon atoms are preferred. Most preferred is methane sulfonic acid which is heated to a temperature in the range from about 100° C. to about 150° C. to cyclize the aminodiol. The reaction occurs over a period of about 10 hr, after which the reaction mixture is cooled down and 10% NaOH is added. Upon working up the mixture to recover the pure polysubstituted morpholine, a colorless oil is usually obtained.

Process for preparing polysubstituted aminodiethers

The aminodiol obtained as described hereinabove may be converted to an aminodiether by reaction with an alkyl iodide or dimethyl sulfate, after first heating the aminodiol to reflux in an aromatic solvent such as toluene, in the presence of a stong base, such as sodium hydride, under an inert atmosphere. The aminodiether obtained may be worked up by adding water, extracting the aqueous solution with toluene, drying the combined toluene solutions with sodium sulfate, and concentrating. The aminodiether is isolated by simple distillation.

The structure of a polysubstituted aminodiether is as follows:

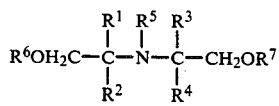

wherein,
R$^1$, R$^2$, R$^3$ and R$^4$ are independently selected from the group consisting of hydrogen, aryl, alkyl having from 1 to about 24 carbon atoms, cycloalkyl having from 5 to about 7 carbon atoms, aralkyl having from 7 to about 20 carbon atoms, cyanoalkyl having from 2 to about 12 carbon atoms, ether having from 4 to about 18 carbon atoms, and hydroxyalkyl having from 2 to about 18 carbon atoms;
R$^1$ and R$^2$ together, or R$^3$ and R$^4$ together, or each pair, may be cyclized forming a ring having from about 5 to about 8 carbon atoms;
except that not more than one of R$^1$, R$^2$, R$^3$ or R$^4$ may be hydrogen, and no more than three of R$^1$, R$^2$, R$^3$ and R$^4$ may be cyclic;
R$^5$ is selected from hydrogen, oxygen and alkyl having from 1 to about 24 carbon atoms;
R$^6$ and R$^7$ are independently selected from the group consisting of alkyl having from 1 to about 24 carbon atoms, and aralkyl having from 7 to about 24 carbon atoms.

The polysubstituted HEAA compounds are generally crystalline solids soluble in acetone, diethyl ether, dioxane, tetrahydrofuran, carbon tetrachloride, chloroform, lower primary alcohols having from 1 to about 6 carbon atoms such as methanol, ethanol and propanol, aromatic hydrocarbons such as benzene and toluene, but much less soluble in aliphatic hydrocarbons such as hexane. Some HEAA-derived compounds are oily lightly colored liquids. Many are quite soluble in water and are especially useful when they are to be dispersed in a latex to be stabilized against u-v light degradation. The alkali metal salts range in color from water-white to brown when pure, but when dispersed in an organic material, particularly in polyolefins, polyamides, and polyvinyl aromatics, at a concentration of less than 5 parts per 100 parts by weight of organic material, the color of the HEAA in the composition is not noticeable.

The amount of the stabilizer employed will vary with the particular material to be stabilized and also the polysubstituted HEAA or HEAA-related stabilizer employed. Generally however, for effective u-v light stabilization of most organic materials, an amount of the stabilizer used is in the range from about 0.001 percent to about 10 percent by weight (% by wt) based on the weight of organic material. In typical stabilized compositions the amount of polysubstituted stabilizer used is in the range from about 0.01 to about 5% by wt.

Compositions of this invention are synthetic resinous materials which have been stabilized to combat the deleterious effects of uv light, thermal or oxidative degradation such as are usually evidenced by discoloration and/or embrittlement. These compositions generally benefit from the inclusion of additional, secondary stabilizers to achieve even greater stability against a combination of actinic light, heat and oxygen. Therefore, in conjunction with the stabilizers of this invention, compositions may include stabilizers against degradation by heat and/or oxygen which secondary stabilizers may be present in the range from about 0.1 part to about 10 parts by weight, and preferably from about 0.2 part to about 5 parts by weight per 100 parts by weight of the organic continuous phase. Several types of known UV secondary stabilizers may be used, such as those disclosed in U.S. Pat. Nos. 3,325,448; 3,769,259; 3,920,659; 3,962,255; 3,966,711; 3,971,757; inter alia.

Organic materials which may be stabilized against uv light, thermal and oxidative degradation, include copolymers of butadiene with acrylic acid, alkyl acrylates or methacrylates, polyisoprene, polychloroprene, and the like; polyurethanes; vinyl polymers known as PVC resins such as polyvinyl chloride, copolymers of vinyl chloride with vinylidene chloride, copolymers of vinyl halide with butadiene, styrene, vinyl esters, and the like; polyamides such as those derived from the reaction of hexamethylene diamine with adipic or sebacic acid; epoxy resins such as those obtained from the condensation of epichlorohydrin with bisphenols, and the like; ABS resins, polystyrene, polyacrylonitrile, polymethacrylates, poly-carbonates, varnish, phenol-formaldehyde resins, polyepoxides, polyesters, and polyolefin homo- and copolymers such as polyethylene, polypropylene, ethylene-propylene polymers, ethylene-propylenediene polymers, ethylene-vinyl acetate polymers, and the like. The polysubstituted HEAA compounds can also be used to stabilize mixtures and blends of polymeric materials such as ABS resin blends, PVC and polymethacrylate blends, and blends of polyolefin homopolymers and copolymers such as blends of polypropylene in epdm polymers.

Most particularly substituted HEAA and HEAA-derived compounds of this invention having at least three and preferably four substituents on the N-adjacent C atoms, including of course if the substituents are cyclized, are especially useful as uv-light-stabilizers for synthetic resinous materials which are at least partially permeable to visible light, and particularly for those which are transparent thereto, such as the polyvinylaromatics and polyolefins. It will be recognized that if each of the substituents $R^1$ and $R^2$ on the N-adjacent C atom are cyclized, and the $R^2$ and $R^3$ substituents of the other N-adjacent C atom are not, then, in the sense used herein, there are still four substituents, as is also the case if the substituents $R^3$ and $R^4$ are cyclized.

Many known compounding ingredients may be used along with the substituted PIP-T stabilizers in the compositions. Such ingredients include metal oxides such as zinc, calcium and magnesium oxide, fatty acids such as stearic and lauric acid, and salts thereof such as cadmium, zinc and sodium stearate and lead oleate; fillers such as calcium and magnesium carbonate, calcium and barium sulfates, aluminum silicates, asbestos, and the like; plasticizers and extenders such as dialkyl and diaryl ogranic acids like diisobutyl, diisooctyl, diisodecyl, and dibenzyl oleates, stearates, sebacates, azelates, phthalates, and the like; ASTM type 2 petroleum oils, paraffinic oils, castor oil, tall oil, glycerin, and the like.

Particularly desirable secondary stabilizers are one or more antioxidants used in the range from about 0.1 part to about 20 parts by weight, preferably from about 0.2 part to about 5 parts by weight per 100 parts by weight of the material. Of the types of antioxidants to be used, are phosphite, phosphate, sulfide and phenolic antioxidants, the last being preferred. Most preferred are phenolic antioxidants such as 2,6-di-t-butyl paracresol; 2,2'-methylene-bis-(6-t-butyl-phenol); 2,2'-thiobis-(4-methyl-6-t-butyl-phenol); 2,2'-methylene-bis-(6-t-butyl-4-ethyl-phenol); 4,4'-butylene-bis-(6-t-butyl-m-cresol); 2-(4-hydroxy-3,5-di-t-butylanilino)-4,6-bis-(octylthio)-1,3,5-triazine; hexahydro-1,3,5-tris-(3,5-di-t-butyl-4-hydroxyphenyl)propionyl-s-triazine; hexahydro-1,3,5-tirs-(3,5-di-t-butyl-4-hydroxybenzyl)-isocyanurate; tetrakismethylene-3-(3',5'-di-t-butyl-4'-hydroxyphenyl)-propionate methane; and other antioxidant synergists such as distearyl thiodipropionate; dilauryl thiodipropionate; tri(nonylphenyl)phosphite; tin thioglycolate; and particularly commercially available antioxidants such as Goodrite® 3114, and 3125, Irganox 1010, 1035, 1076 and 1093. Other ingredients such as pigments, tackifiers, flame retardants, fungicides, and the like may also be added.

The polysubstituted HEAA stabilizers, and the other compounding ingredients if used, can be admixed with organic materials using known mixing techniques and equipment such as internal mixing kettles, a Banbury mixer, a Henschel mixer, a two-roll mill, an extruder mixer, or other standard equipment, to yield a composition which may be extruded, pressed, blowmolded or the like into film, fiber or shaped articles. Usual mixing times and temperatures can be employed which may be determined with a little trial and error for any particular compositions. The objective is to obtain intimate and uniform mixing of the components. A favorable mixing procedure to use when adding a polysubstituted HEAA to an organic material is either to dissolve or suspend the compound in a liquid such as hexane or benzene before adding it, or to add the HEAA directly to the polymeric organic material whether the HEAA is in the form of a powder or oil, or to extruder-mix the HEAA and the polymeric material prior to forming the product.

The u-v stability of a particular composition containing a polymeric material and a polysubstituted HEAA can be evalutated by exposing a prepared sample of the composition to Xenon or carbon arc light in a Weather-O-meter operating at a temperature, for example, about 140° F. (60° C.). Degradation of the sample can be followed by periodically measuring tensile strength left, and the hydroperoxide absorption band at $3460\ cm^{-1}$ or carbonyl absorption band at $1720\ cm^{-1}$ using an IR spectrophotometer. The rapid formation of carbonyl indicates failure of the sample. The test procedure is well known, and is published in the text *Photodegradation, Photo-oxidation and Photostabilization of Polymers* by Ranby and Rabek, John Wiley & Sons, New York, N.Y. (1975), at pages 129 et seq., and is disclosed in U.S. Pat. No. 3,909,493. Failure of the sample is also checked by visual signs of cracking when the sample is bent 180°.

Samples of the compositions can also be checked for oxidative and thermal stability by measuring the time to discoloration and/or embrittlement of the sample after aging in an air circulating oven at 140° C., and other standard ASTM tests.

The following Table I sets forth data obtained in tests conducted with 2 mil thickness samples of polyproylene. The blank and each sample includes 0.05 parts per hundred parts of resin ('phr') of Goodrite* 3125 antioxidant, and the amount of stabilizer used in each sample is stated. Oven aging is done continuously at 125° C. in the standard test procedure, and the Weather-O-Meter tests give the number of hours after which a sample loses 50% of its tensile strength. Test compositions of this invention were removed from the oven after having withstood 33 days, and were removed from the Weather-O-Meter after having withstood more than 2000 hr without losing 50% of their tensile strength. The results documented simply indicate that the samples withstood more than 33 days of oven aging, and more than 2000 Weather-O-Meter exposure. Chimasorb ® 944 is a commercially available polytriazine having piperidine substituents disclosed in U.S. Pat. No. 4,086,204. Cyasorb ® 531 is also a commercially available stablizer (from American Cyanamid Co.) having a benzophenone structure.

TABLE I

| Ex. | Stabilizer used | Amount (phr) | Oven aging (days) | Failure* (hr) |
|---|---|---|---|---|
| 1 | Blank | 0 | 25 | 870 |
| 2 | Cyasorb 531 | 0.1 | 25 | 1760 |
| 3 | Chimasorb 944 | 0.1 | 25 | 1860 |
| 4 | sodium tetramethyl-hydroxyethylamino acetate ("4M-HEAA") | 0.1 | 33 | >2000 |
| 5 | 3,3,5,5-tetramethyl-2-morpholone | 0.1 | 33 | >2000 |
| 6 | 3,3-pentamethylene-5,5-dimethyl-2 morpholone | 0.1 | 33 | >2000 |
| 7 | 3-ethyl-3,5,5-trimethyl-2-morpholone | 0.1 | 33 | >2000 |
| 8 | di-(1-hydroxy-2-methyl-2-propyl)amine | 0.1 | 33 | >2000 |
| 9 | 3,3,5,5-tetramethyl-morpholine | 0.1 | 33 | >2000 |

*tensil strength was about 50% of original

EXAMPLE 1

A. Preparation of sodium tetramethyl-hydroxyethylaminoacetate ("4M-HEAA") having the structure:

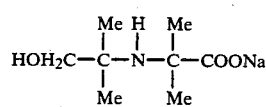

Me = methyl 2-amino-2-methyl-propanol (0.6 mole), chloroform (0.8 mole), acetone (2.4 mole) and benzyltriethylammonium chloride (0.018 mole) are placed in a three-necked flask cooled in a circulating ice bath so that the temperature is maintained in the range from about 0°–5° C. Aqueous sodium hydroxide (50% solution) is added dropwise into the contents of the flask while they are stirred. It is preferred to add at least four moles of NaOH for each mole of 2-amino-2-methyl-1-propanol, and a substantial excess over four equivalents is best. Also, in excess of one equivalent of chloroform is used, and nearly two equivalents is better. The phase transfer catalyst may be dispensed with in some instances if a very large excess of ketone is used as a reactant.

Stirring is continued overnight and the reaction mixture is filtered. The solid recovered is a mixture of 4M-HEAA and NaCl, but some of each may still be present in the filtrate. The organic phase is separated from the aqueous phase of the filtrate, and the ketone is recovered from the organic phase. If there is any 4M-HEAA in either the organic or aqueous phases, it may be recovered therefrom in any conventional manner. The solid is rinsed with methylene chloride to dissolve remaining organic phase on the solids which are then stirred into 300 ml methanol in which the 4M-HEAA dissolves but the NaCl does not. Crude 4M-HEAA is recovered from the methanol as a solid. Upon analysis, it is confirmed that the solid obtained is sodium tetramethyl-hydroxyethylaminoacetate.

The compound 4M-HEAA is found to have excellent stabilization properties against u-v light degradation as is evident from the test results when it is incorporated in polypropylene, which results are set forth in Table I hereinbefore.

B. Preparation of sodium 2-[2-methyl-1-hydroxy-2-propylamino]-2-butanoate:

In a manner analogous to that described in example 1A hereinabove, 2-butanone is substituted for acetone, and the reaction similarly carried out. Analysis of the product confirms its identification hereinabove.

C. Preparation of sodium 2-[2-methyl-1-hydroxy-2-propylamino]-2-cyclohexyl carboxylate having the following structure:

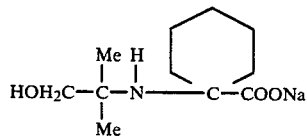

In a manner analogous to that described in example 1A hereinabove, cyclohexanone is substituted for acetone, and the reaction similarly carried out. The product obtained is identified as one having the structure written hereinabove.

EXAMPLE 2

A. Preparation of 3,3,5,5-tetramethyl-2-morpholone having the structure:

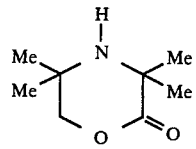

The crude 4M-HEAA obtained in example 1A hereinabove was refluxed with concentrated HCl (500 ml) for 15 hr and then the HCl is removed in a rotary evaporator, to yield a solid 2-morpholone-hydrochloride. Since the 2-morpholone-hydrochloride still contains small amounts of water, toluene (600 ml) is added and the mixture was refluxed with a Dean-Stark trap to remove all the water. Thereafter, triethylamine (0.9 mole) was added and the mixture refluxed under argon for 10 hr to remove the HCl attached to the 2-morpholone so as to form the compound having the above-identified structure which compound is recovered in better than 75% yield as a colorless oil. From the results set forth in Table I hereinbefore it is evident that the oil has excellent u-v light stabilization characteristics.

B. Preparation of 3-ethyl-3,5,5-trimethyl-2-morpholone:

In a manner analogous to that described in example 2A hereinabove, the sodium 2-[2-methyl-1-hydroxy-2-propylamino]-2-butanoate prepared in example 1B is converted with about 75% yield to a pale oily liquid which, upon analysis, is confirmed as having the structure written immediately hereinabove.

C. Preparation of 3,3-pentamethylene-5,5-dimethyl-2-morpholone having the structure:

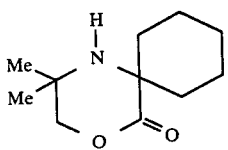

In a manner analogous to that described in example 2A hereinabove, the sodium 2-[2-methyl-1-hydroxy-2-propylamino]-2-cyclohexyl carboxylate prepared in example 1C is converted with about 75% yield to a water-white oily liquid which upon analysis, is found to have the structure written immediately hereinabove.

EXAMPLE 3

A Preparation of di-(1-hydroxy-2-methyl-2-propyl)amine having the structure:

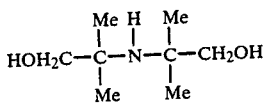

0.2 mole of tetramethyl-2-morpholone prepared as described in example 2A hereinabove, and 200 ml tetrahydrofuran (THF) were placed in a three-necked flask under argon. Lithium aluminum hydride (0.2 mole) was added in small portions during a half hour period, after which the reaction mixture was refluxed for 5 hr, then cooled down. 8 ml of 10% NaOH followed by 23 ml distilled water are added with stirring, and the mixture was filtered. The solid obtained was rinsed thoroughly with THF and the filtrate concentrated. The essentially pure aminodiol is obtained upon recrystallization or distillation, which has a 90% yield, and it has a m p of 73°75° C. Upon analysis it is confirmed that it has the structure written hereinabove.

As is evident from Table I hereinbefore, the aminodiol has excellent u-v light stabilization properties.

B. Preparation of (1-hydroxy-2-methyl-2-propyl)(1-hydroxy-2-methyl-2-butyl)amine:

In a manner analogous to that described in example 3A hereinabove, 3-methyl,3-ethyl-5,5-dimethyl-2-morpholone is reduced with LiAlH$_4$ to provide a better than 80% yield of (1-hydroxy-2-methyl-2-propyl)(1-hydroxy-2-methyl-2-butyl)amine which has a b p of 136°-7° C./4 mm Hg.

C. Preparation of (1-hydroxy-2-methyl-2-propyl)(1-hydroxymethyl-1-cyclohexyl)amine:

In a manner analogous to that described in example 3A hereinabove, 3,3-pentamethylene-5,5-dimethyl-2-morpholone is reduced with LiAlH$_4$ to provide a better than 75% yield of (1-hydroxy-2-methyl-2-propyl)(1-hydroxymethyl-1-cyclohexyl)amine.

EXAMPLE 4

A. Preparation of tetramethyl-monoaza-15-crown-5.

A small amount of metallic sodium is added to 0.033 mole of di-(1-hydroxy-2-methyl-2-propyl)amine dissolved in t-butanol (250 ml) and triethylene glycol ditosylate (0.033 mole) in p-dioxane (150 ml) was added in drops during a 3 hr period at a temperature of 60° C. After the addition, the reaction mixture was filtered and the solvent was evaporated. Water was added to the residue and the solution was extracted with several aliquots of methylene chloride. The mixture was then dried and concentrated. Upon distillation pure tetramethyl-monoaza-15-crown-5 is obtained (n=3 ethylene oxide units) in better than 50% yield and has a b p of 97°-9° C./0.15 mm Hg.

B. Preparation of trimethyl-ethyl-monoaza-15-crown-5.

In a manner analogous to that described in example 6A hereinabove, (1-hydroxy-2-methyl-2-propyl)(1-hydroxy-2-methyl-2-butyl)amine is reacted with triethylene glycol ditosylate, and the reaction mixture worked up to yield about a 50% yield of a colorless oil having a b p of 122°-4° C./0.08 mm. The structure of the oil is confirmed by the usual analysis (n=3 ethylene oxide groups).

C. Preparation of dimethyl-pentamethylene-monoaza-15-crown-5.

In a manner analogous to that described in example 6A hereinabove, (1-hydroxy-2-methyl-2-propyl)(1-hydroxymethyl-1-cyclohexyl)amine is reacted with triethylene glycol ditosylate and the reaction mixture worked up to give about a 50% yield of a colorless oil having a b p of 143°-6° C./0.1 mm. The structure of the compound is confirmed by analysis (n=3 ethylene oxide units).

D. Preparation of tetramethyl-18-crown-6.

In manner analogous to that described in example 6A hereinabove, a small amount of potassium metal was used instead of sodium; di-(1-hydroxy-2-methyl-2-propyl)amine was reacted with tetraethylene glycol ditosylate, the reaction mixture worked up as before, and a colorless oil was obtained in about 40% yield which oil had a b p of 120°-3° C./0.1 mm. Upon analysis the oil is found to be tetramethyl-18-crown-6 (n=4 ethyleneoxide units).

E. Preparation of tetramethyl-12-crown-4.

In a manner analogous to that described in example 6A hereinabove, a small amount of lithium metal is used instead of sodium, and di-(1-hydroxyl-2-methyl-2-propyl)amine is reacted with diethylene glycol ditosylate. The reaction mixture is worked up as before to give about a 15% yield of tetramethyl-12-crown-4 (n=2 ethylene oxide units) which oil has a b p of 68°-9° C./0.2 mm.

All the crown ethers prepared hereinabove are found to have excellent u-v stabilization properties.

EXAMPLE 5

A. Preparation of 3,3,5,5-tetramethyl-morpholine.

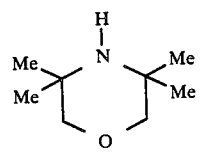

3.0 g of di-(1-hydroxy-2-methyl-2-propyl)amine and 25 ml of methanesulfonic acid are placed in a round-bottomed flask and heated to 130° C. for more than 10 hr after which the reaction mixture is cooled down and added slowly to a 10% NaOH solution. The mixture is then extracted with 50 ml aliquots of methylene chloride several times, dried and concentrated. Upon distillation, a colorless oil is obtained in about 50% yield which boils at 63°-4° C./19 mm. It is found to be an excellent u-v stabilizer, as is evident from the data in Table I. Analysis by proton nuclear magnetic resonance (nmr) and field desorption (FD) mass spectroscopy confirms the structure of the oil as being 3,3,5,5-tetramethyl-morpholine.

B. Preparation of 3,5,5-trimethyl-3-ethyl-morpholine.

In a manner analogous to that described in example 5A hereinabove, starting with (1-hydroxy-2-methyl-2-propyl)(1-hydroxy-2-methyl-2-butyl)amine and reacting with methanesulfonic acid, then working up the reaction mixture, a colorless oil having a b p 71°–3° C./20 mm, is obtained in about 50% yield. Less than 5% by weight of the oil is found to provide excellent u-v light stability in polypropylene.

C. Preparation of 3,3-dimethyl-5,5-pentamethylene-morpholine.

In a manner analogous to that described in example 5A hereinabove, (1-hydroxy-2-methyl-2-propyl)(1-hydroxymethyl-1-cyclohexyl)amine is reacted with methanesulfonic acid and worked up to obtain about a 50% yield of colorless oil having a b p 86°–9° C./3 mm. Its structure is confirmed by GC, IR and proton nmr analysis. About 0.5–1.0% by weight in polypropylene is found to provide excellent u-v stability.

EXAMPLE 6

A. Preparation of N,N'-bis-(1-methoxy-2-methyl-2-propyl)-amine having the structure:

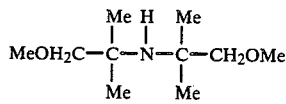

Sodium hydride (0.24 mole) is washed once with dry toluene, then suspended in 100 ml toluene. Di-(1-hydroxy-2-methyl-2-propyl)amine (0.1 mole) is added and the mixture is slowly warmed to reflux under argon. After about 1 hr the mixture is cooled down to room temperature and an alkylating agent such as methyl iodide or dimethyl sulfate (0.22 mole) in 20 ml of toluene is added dropwise over a period of about 1 hr. The reaction is stirred at ambient temperature overnight, and worked up by adding water, extracting the aqueous solution with toluene, drying the combined toluene solutions with sodium sulfate, and concentrating. The desired N,N'-bis-(1-methoxy-2-methyl-2-propyl)-amine is obtained in pure form by simple distillation, with about a 90% yield. It has a b p of 80°–2° C./10 mm Hg.

In a manner analogous to that described in example 6A hereinabove, the following aminodiethers are prepared by reacting the appropriate aminodiol and alkylating agent, respectively, and working up as described to obtain about 80% or better yields of the aminodiethers: N-(1-methoxy-2-methyl-2-propyl)-N'-(1-methoxy-2-methyl-2-butyl)amine has a b p of 91°–4° C./10 mm., and, N-(1-methoxy-2-methyl-2-propyl)-N'-[2-(methoxymethyl)cyclohexyl] amine has a b p of 111°–4° C./2 mm.

Corresponding nitroxyl compounds of the foregoing compounds may be prepared by conventional procedures such as the one described in *Synthetic Communications*, 5, 409 (1975). The nitroxyl is generally a orange-red colored oil showing a typical 3-line structure in elctron-spin resonance (esr) spectroscopy.

EXAMPLE 7

Process for preparation of polysubstituted 2-morpholones, whether prior art or novel compounds, and particularly tetra-substituted 2-morpholones:

The first step in the process of this invention is to prepare a 4M-HEAA having the desired substituents. It will be appreciated that these substituents are most conveniently provided by reacting a 2,2'-substituted-2-aminoethanol and a monoketone with appropriate substituents on either side of the carbonyl C, or benzaldehyde which may have ring substituents. As described in Example 1 hereinbefore, the 4M-HEAA is formed by reacting the aforesaid appropriately substituted reactants in the presence of chloroform and, preferably, in the presence of a phase transfer catalyst. In general, the 4M-HEAA is formed with no substituent on the N atom. The 4M-HEAA is then cyclized in the presence of a concentrated mineral acid as described in Example 2 hereinbefore to form a polysubstituted 2-morpholone having the general structure:

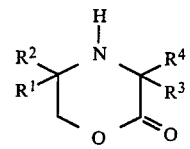

wherein, $R^1$, $R^2$, $R^3$ and $R^4$ are independently selected from the group consisting of aryl, alkyl having from 1 to about 24 carbon atoms, cycloakyl having from 5 to about 7 carbon atoms, aralkyl having from 7 to about 20 carbon atoms, cyanoalkyl having from 2 to about 12 carbon atoms, ether having from 4 to about 18 carbon atoms, and hydroxyalkyl having from 1 to about 18 carbon atoms; and, $R^1$ and $R^2$ together, or $R^3$ and $R^4$ together, or each pair, may be cyclized forming a ring having from about 5 to about 8 carbon atoms;

except that not more than one of $R^1$, $R^2$, $R^3$ or $R^4$ maybe hydrogen; and no more than three of $R^1$, $R^2$, $R^3$ and $R^4$ may be cyclic.

The N atom may be substituted, if desired, with a substituent $R^5$ selected from the group consisting of O, lower alkyl having from 1 to about 6 carbon atoms, and hydroxyalkyl having from 1 to about 6 carbon atoms. Such substitution is preferably effected soon after formation of the 4M-HEAA, before it is cyclized, since in most instances, making the substitution after the 2-morpholone is formed, is more difficult because of the hindrance of the substituents on the N-adjacent C atoms. As will be evident upon consideration of the problem posed by the highly hindered nature of the N atom, particularly if it is tetra-substituted rather than only tri-substituted, it is surprising that cyclization of the 4M-HEAA is effected at all by the mineral acid.

A. Preparation of 5,5-dimethyl-3-phenyl-2-morpholone:

In a manner analogous to that described in Example 1A hereinbefore, 2-amino-2-methyl-1-propanol, benzaldehyde and chloroform are reacted at ice bath temperature in the presence of a phase transfer catalyst and aqueous NaOH is added dropwise into the reaction vessel while the contents are being stirred. The sodium salt of the compound is recovered with an analogous workup, and warmed with a mineral acid to yield a compound which is a hydrochloride. When the hydrochloride is reacted with triethanolamine, the compound recovered is identified as being 5,5-dimethyl-3-phenyl-2-morpholone.

B. Preparation of [2'-(2'-cyanopropyl)]-3,5,5-trimethylmorpholin-2-one:

In a manner analogous to that described in Example 1A hereinbefore, 2-amino-1-propanol, chloroform and 4-cyano-4-methyl-2-butanone are reacted in the presence of a phase transfer catalyst with the addition of aqueous NaOH (50% solution) to form a sodium salt which is recovered and warmed with conc HCl to form the morpholone hydrochloride to which triethanolamine is added so as to yield a compound which is identified as being [2'-(2'-cycanopropyl)]-3,5,5-trimethylmorpholin-2-one.

C. Preparation of 5-methyl-3-phenyl-3-ethyl-2-morpholone:

In a manner analogous to that described in Example 1A hereinabove, 2-amino-1-propanol, chloroform and phenylethylketone are reacted to yield a sodium salt which is recovered and cyclized with conc HCl to yield a morpholone hydrochloride which upon reaction with triethanolamine yields a compound identified as being 5-methyl-3-phenyl-3-ethyl-2-morpholone.

D. Preparation of 3-[2-(2'-cyanopropyl)]-3,5-dimethyl-hydroxyethyl-morpholin-2-one:

In a manner analogous to that described in Example 1A hereinbefore, 2-amino-2-methyl-1,3-propanediol is reacted with 4-cyano-4-methyl-2-butanone and chloroform, optionally in the presence of a phase transfer catalyst, with the addition of aqueous NaOH solution, to yield a sodium salt. The salt is cyclized upon warming with conc HCl to yield a polysubstituted morpholone hydrochloride which upon reaction with triethanolamine yields a compound identified as being 3-[2-(2'-cyanopropyl)1-3,5-dimethyl-hydroxyethyl-morpholin-2-one.

E. Preparation of 5-hydroxymethyl-3,3,5-trimethyl-2-morpholone represented by the structure:

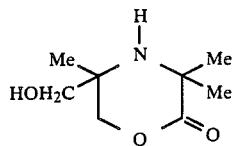

In a manner analogous to that described in Example 1A hereinbefore, 2-amino-2-methyl-1,3-propanediol is reacted with chloroform in excess, and acetone in large excess, optionally in the presence of a phase transfer catalyst, with the addition of aqueous NaOH solution, to yield a sodium salt. The salt is cyclized upon warming with conc HCl to yield a polysubstituted morpholone hydrochloride which upon reaction with triethanolamine yields a compound identified as having the structure given immediately hereiabove.

F. Preparation of 5-hydroxymethyl-5-ethyl-3,3-dimethyl-2-morpholone:

In a manner analogous to that described in Example 1A hereinbefore, the reaction of 2-amino-2-ethyl-1,3-propanediol with chloroform in excess, and with acetone in large excess, with the addition of aqueous NaOH solution, yields a sodium salt which is cyclized with conc HCl to yield the compound identified as having the structure given immediately hereinabove.

I claim:

1. A polysubstituted 2-morpholine having the structure:

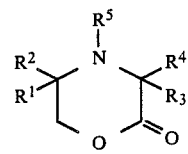

wherein,

R$^1$, R$^2$, R$^3$ and R$^4$ are independently alkyl having from 1 to about 24 carbon atoms;

R$^5$ is selected from hydrogen, oxygen, hydroxyl and alkyl having from 1 to about 24 carbon atoms.

2. The polysubstituted 2-morpholone of claim 1 selected from the group consisting of:
3,3,5,5-tetramethyl-2-morpholone; and,
3-ethyl-3,5,5-trimethyl-2-morpholone.

* * * * *

UNITED STATES PATENT AND TRADEMARK OFFICE
CERTIFICATE OF CORRECTION

PATENT NO. : 4,528,370
DATED : July 9, 1985
INVENTOR(S) : JOHN TA-YUAN LAI

It is certified that error appears in the above-identified patent and that said Letters Patent are hereby corrected as shown below:

In claim 1, line 1 the word "2-morpholine" should read --2-morpholone--.

Signed and Sealed this

First Day of October 1985

[SEAL]

Attest:

Attesting Officer

DONALD J. QUIGG

*Commissioner of Patents and Trademarks—Designate*